United States Patent [19]
Lyssikatos et al.

[11] Patent Number: 6,080,769
[45] Date of Patent: Jun. 27, 2000

[54] IMIDAZOLIDIN-4-ONE DERIVATIVES USEFUL AS ANTICANCER AGENTS

[75] Inventors: Joseph P. Lyssikatos, Gales Ferry; Bingwei V. Yang, Waterford, both of Conn.

[73] Assignee: Pfizer Inc., New York, N.Y.

[21] Appl. No.: 09/221,946

[22] Filed: Dec. 28, 1998

Related U.S. Application Data

[60] Provisional application No. 60/070,010, Dec. 30, 1997.

[51] Int. Cl.$^7$ .......................... A01N 43/50; A01N 43/64; A01N 43/82; C07D 403/14; C07D 403/02
[52] U.S. Cl. .......................... 514/359; 514/361; 514/385; 514/400; 514/402; 546/272.7; 548/312.7; 548/316.4
[58] Field of Search .............................. 548/312.7, 316.4; 546/272.7; 514/359, 361, 385, 396, 400, 402

[56] References Cited

FOREIGN PATENT DOCUMENTS

| | | |
|---|---|---|
| WO93/14085 | 7/1993 | WIPO . |
| WO95/23141 | 8/1995 | WIPO . |
| WO96/40142 | 12/1996 | WIPO . |
| WO97/00675 | 1/1997 | WIPO . |
| WO97/13771 | 4/1997 | WIPO . |
| WO97/49700 | 12/1997 | WIPO . |

OTHER PUBLICATIONS

Nancy E. Kohl, et al., "Selective Inhibition of ras–Dependent Transformation by Farnesyltransferase Inhibitor", *Science*, vol. 260, pp. 1934–1937, (1993).

*Primary Examiner*—Alan L. Rotman
*Assistant Examiner*—Rita Desai
*Attorney, Agent, or Firm*—Peter C. Richardson; Paul H. Ginsburg; E. Victor Donahue

[57] ABSTRACT

The present invention relates to compounds of formula 1

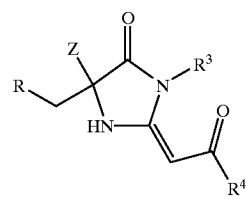

and to pharmaceutically acceptable salts and solvates thereof, wherein Z, R, $R^3$ and $R^4$ are as defined herein. The invention also relates to pharmaceutical compositions containing the compounds of formula 1 and to methods of inhibiting abnormal cell growth, including cancer, in a mammal by administering the compounds of formula 1 to said mammal.

9 Claims, No Drawings

IMIDAZOLIDIN-4-ONE DERIVATIVES USEFUL AS ANTICANCER AGENTS

The present application claims priority under 35 USC section 119 of U.S. provisional application 60/070,010, filed Dec. 30, 1997.

BACKGROUND OF THE INVENTION

This invention relates to a series of novel imidazolidin-4-one derivatives that are useful in the treatment of hyperproliferative diseases, such as cancers, in mammals. This invention also relates to a method of using such compounds in the treatment of hyperproliferative diseases in mammals, especially humans, and to pharmaceutical compositions containing such compounds.

Compounds that are useful in the treatment of hyperproliferative diseases are also disclosed in the following co-pending patent applications: PCT international patent application number PCT/IB97/00675, which designates the United States and was filed on Jun. 11, 1997; U.S. provisional patent application No. 60/041846 (filed Apr. 9, 1997); U.S. provisional patent application No. 60/031862 (filed Nov. 27, 1996); U.S. provisional patent application No. 60/028881 (filed Oct. 17, 1996); PCT international patent application number PCT/IB97/00584, which designates the United States and was filed on May 22, 1997; U.S. patent application Ser. No. 08/653,786 (filed May 28, 1996); PCT international patent application publication number WO 96/40142, which designates the United States and was published on Dec. 19, 1996; PCT international patent application publication number WO 97/13771, which designates the United States and was published on Apr. 17, 1997; PCT international patent application publication number WO 95/23141, which designates the United States and was published on Aug. 31, 1995; U.S. provisional patent application Ser. No. 60/020696 (filed Jun. 27, 1996); International Patent Application PCT/US92/11292, which designates the United States and was published on Jul. 22, 1993 as WO 93/14085; U.S. Pat. No. 4,876,259, which issued on Oct. 24, 1989; International Patent Application PCT/IB95/00189, which designates the United States and was filed on Mar. 20, 1995; U. S. patent application Ser. No. 08/236,743, which was filed on Apr. 29, 1994.

Oncogenes frequently encode protein components of signal transduction pathways which lead to stimulation of cell growth and mitogenesis. Oncogene expression in cultured cells leads to cellular transformation, characterized by the ability of cells to grow in soft agar and the growth of cells as dense foci lacking the contact inhibition exhibited by non-transformed cells. Mutation and/or overexpression of certain oncogenes is frequently associated with human cancer.

To acquire transforming potential, the precursor of the Ras oncoprotein must undergo farnesylation of the cysteine residue located in a carboxyl-terminal tetrapeptide. Inhibitors of the enzyme that catalyzes this modification, farnesyl protein transferase, have therefore been suggested as agents to combat tumors in which Ras contributes to transformation. Mutated, oncogenic forms of Ras are frequently found in many human cancers, most notably in more than 50% of colon and pancreatic carcinomas (Kohl et al., *Science*, Vol. 260, 1834 to 1837, 1993). The compounds of the present invention exhibit activity as inhibitors of the enzyme farnesyl protein transferase and are therefore believed to be useful as anti-cancer and anti-tumor agents.

SUMMARY OF THE INVENTION

The present invention relates to compounds of formula 1

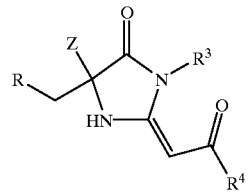

1 and to pharmaceutically acceptable salts and solvates thereof, wherein:

Z is —$(CH_2)_n$-(imidazol-1-yl) wherein n is 1 or 2 or Z is a group of the formula

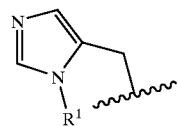

R is pyridin-4-yl or a group of the formula

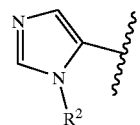

$R^1$ and $R^2$ are each independently selected from the group consisting of H, $C_1$–$C_{10}$ alkyl, —$OR^6$, —$C(O)(C_1$–$C_{10}$ alkyl), —$(CH_2)_t(C_6$–$C_{10}$ aryl), —$(CH_2)_t$(5–10 membered heterocyclic), —$C(O)(CH_2)_t(C_6$–$C_{10}$ aryl), —$(CH_2)_tO(CH_2)_j(C_6$–$C_{10}$ aryl), —$C(O)(CH_2)_t$(5–10 membered heterocyclic), —$SO_2(CH_2)_t(C_6$–$C_{10}$ aryl), or —$SO_2(CH_2)_t$(5–10 membered heterocyclic), wherein j is an integer ranging from 0 to 2, t is an integer ranging from 0 to 5, the —$(CH_2)_t$— moieties of the foregoing $R^1$ and $R^2$ groups optionally include a carbon—carbon double or triple bond where t is an integer between 2 and 5, and the foregoing $R^1$ and $R^2$ groups, other than H, are optionally substituted by 1 to 3 $R^5$ substituents;

$R^3$ is —$(CH_2)_m$(1- or 2-adamantyl), —$(CH_2)_m(C_6$–$Cl_{10}$ aryl), $C_1$–$C_{15}$ alkyl,

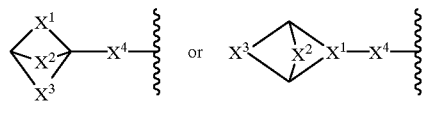

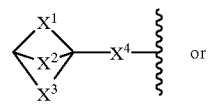

-continued

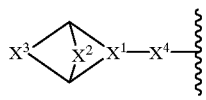
3 wherein m is an integer ranging from 0 to 6;

$X^1$, $X^2$, and $X^3$ are each independently $C_1$–$C_7$ alkylene optionally containing 1 or 2 double or triple bonds where said alkylene contains at least two carbon atoms, $X^4$ is a bond or $C_1$–$C_7$ alkylene optionally containing 1 or 2 double or triple bonds where said alkylene contains at least two carbon atoms, and, in formula 3, the $X^4$ moiety is attached to the $X^1$ moiety at any available carbon in the $X^1$ moiety's alkylene chain;

$R^4$ is $C_1$–$C_6$ alkyl, —$(CH_2)_t(C_6$–$C_{10}$ aryl), or —$(CH_2)_t$ (5–10 membered heterocyclic), wherein said t is an integer ranging from 0 to 5 and said $R^4$ groups are optionally substituted by 1 to 3 $R^5$ substituents;

each $R^5$ is independently selected from the group consisting of halo, nitro, cyano, —$C(O)OR^6$, —$SO_2NR^6R^8$, —$NR^6R^8$, —$C(O)R^6$, —$OR^6$, —$C(O)NR^6R^8$, —$OC(O)NR^6R^8$, —$NR^8C(O)NR^8R^6$, —$NR^8C(O)R^6$, —$NR^8C(O)O(C_1$–$C_6$ alkyl), —$C(NR^8)NR^8R^6$, —$C(NCN)NR^8R^6$, —$C(NCN)S(C_1$–$C_6$ alkyl), —$NR^8C(NCN)S(C_1$–$C_6$ alkyl), —$NR^8C(NCN)NR^8R^6$, —$NR^8SO_2(C_1$–$C_6$ alkyl), —$S(O)_n(C_1$–$C_6$ alkyl) wherein n is an integer ranging from 0 to 2, —$NR^8C(O)C(O)NR^8R^6$, —$NR^8C(O)C(O)R^8$, —$SO_2$ ($C_6$–$C_{10}$aryl), —$SO_2$(5–10 membered heterocyclic), $C_6$–$C_{10}$ aryl, 5–10 membered heterocyclic, and $C_1$–$C_4$ alkyl optionally substituted by 1 to 3 fluoro substituents, wherein the aryl and heterocyclic moieties of said $C_6$–$C_{10}$ aryl, 5–10 membered heterocyclic, —$SO_2(C_6$–$C_{10}$ aryl) and —$SO_2$(5–10 membered heterocyclic) groups are optionally substituted by 1 or 2 groups independently selected from halo, nitro, cyano, —$C(O)OR^6$, —$SO_2NR^6R^8$, —$NR^6R^8$, —$C(O)$ $R^6$, —$OR^6$, and —$S(O)_n(C_1$–$C_6$ alkyl) wherein n is 0 to 2;

each $R^6$ is independently hydrogen or $C_1$–$C_6$ alkyl;

each $R^7$ is independently selected from cyano, —$OR^6$, —$OC(O)R^6$, —$C(O)OR^6$, —$C(O)NR^6R^8$, —$NR^6R^8$, —$SO_2NR^6R^8$, and $C_1$–$C_6$ alkyl optionally substituted by hydroxy or up to three halo groups;

and, each $R^8$ is independently $R^6$ or —$OR^6$.

Preferred compounds of formula 1 include those wherein Z is a group of the formula

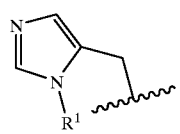

R is a group of the formula

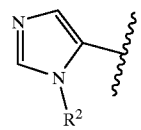

and $R^1$ and $R^2$ are each independently selected from H and $C_1$–$C_6$ alkyl.

Other preferred compounds formula 1 include those wherein $R^3$ is a moiety of formula 2 or 3. More preferred are those compounds in which $R^3$ is 2,6,6-trimethyl-bicyclo [3.1.1]hept-3-ylmethyl.

Other preferred compounds of formula 1 include those wherein $R^4$ is phenyl optionally substituted by 1 to 3 $R^5$ substituents.

Specific preferred compounds include the following:

4-{[4,4-Bis-(1H-imidazol-4-ylmethyl)-5-oxo-1-((−)-(2,6,6-trimethyl-bicyclo[3.1.1]hept-3-ylmethyl))-imidazolidin-2-ylidene]-acetyl}-benzonitrile;

4-{[4,4-Bis-(3-methyl-3H-imidazol-4-ylmethyl)-5-oxo-1-(2,6,6-trimethyl-bicyclo[3.1.1]hept-3-ylmethyl)-imidazolidin-2-ylidene]-acetyl}-benzonitrile;

4-{[4,4-Bis-(1H-imidazol-4-ylmethyl)-5-oxo-1-((+)-(2,6,6-trimethyl-bicyclo[3.1.1]hept-3-ylmethyl))-imidazolidin-2-ylidene]-acetyl}-benzonitrile;

4-{[4-(2Imidazol-1-yl-ethyl)-5-oxo-4-pyridin-4-ylmethyl-1-((+)-(2,6,6-trimethyl-bicyclo[3.1.1]hept-3-ylmethyl))-imidazolidin-2-ylidene]-acetyl}-benzonitrile;

4-{[1-Adamantan-1-ylmethyl-4,4-bis-(3-methyl-3H-imidazol-4-ylmethyl)-5-oxo-imidazolidin-2-ylidene]-acetyl}-benzonitrile;

and the pharmaceutically acceptable salts and solvates of the foregoing compounds.

This invention also relates to a method of inhibiting abnormal cell growth in a mammal, including a human, comprising administering to said mammal an amount of a compound of the formula 1, as defined above, or a pharmaceutically acceptable salt or solvate thereof, that is effective in inhibiting farnesyl protein transferase.

This invention also relates to a method of inhibiting abnormal cell growth in a mammal, including a human, comprising administering to said mammal an amount of a compound of the formula 1, as defined above, or a pharmaceutically acceptable salt or solvate thereof, that is effective in inhibiting abnormal cell growth.

The invention also relates to a method for the inhibition of abnormal cell growth in a mammal which comprises administering to said mammal a therapeutically effective amount of a compound of formula 1, or a pharmaceutically acceptable salt or solvate thereof, in combination with an anti-tumor agent selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, anti-hormones, and anti-androgens.

This invention also relates to a pharmaceutical composition for inhibiting abnormal cell growth in a mammal, including a human, comprising an amount of a compound of the formula 1, as defined above, or a pharmaceutically acceptable salt or solvate thereof, that is effective in inhibiting farnesyl protein transferase, and a pharmaceutically acceptable carrier.

This invention also relates to a pharmaceutical composition for inhibiting abnormal cell growth in a mammal, including a human, comprising an amount of a compound of the formula 1, as defined above, or a pharmaceutically acceptable salt or solvate thereof, that is effective in inhibiting abnormal cell growth, and a pharmaceutically acceptable carrier.

The invention also relates to a pharmaceutical composition for the inhibition of abnormal cell growth in a mammal which comprises a therapeutically effective amount of a compound of formula 1, or a pharmaceutically acceptable salt or solvate thereof, in combination with a pharmaceutically acceptable carrier and an anti-tumor agent selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, anti-hormones, and anti-androgens. "Abnormal cell growth", as used herein, refers to cell growth that is independent of normal regulatory mechanisms (e.g., loss of contact inhibition). This includes the abnormal growth of: (1) tumor cells (tumors) expressing an activated Ras oncogene; (2) tumor cells in which the Ras protein is activated as a result of oncogenic mutation in another gene; and (3) benign and malignant cells of other proliferative diseases in which aberrant Ras activation occurs. Examples of such benign proliferative diseases are psoriasis, benign prostatic hypertrophy and restenosis.

The term "halo", as used herein, unless otherwise indicated, means fluoro, chloro, bromo or iodo. Preferred halo groups are fluoro, chloro and bromo.

The term "alkyl", as used herein, unless otherwise indicated, includes saturated monovalent hydrocarbon radicals having straight, cyclic or branched moieties.

The term "alkoxy", as used herein, unless otherwise indicated, includes O-alkyl groups wherein "alkyl" is defined above.

The term "aryl", as used herein, unless otherwise indicated, includes an organic radical derived from an aromatic hydrocarbon by removal of one hydrogen, such as phenyl or naphthyl.

The term "pinane", as used herein, unless otherwise indicated, includes 2,6,6,-trimethyl-bicyclo[3.1.1.]hept-3-yl.

The term "heterocyclic", as used herein, unless otherwise indicated, includes aromatic and non-aromatic heterocyclic groups containing one to four heteroatoms each selected from O, S and N. Such heterocyclic groups include benzo-fused ring systems, ring systems substituted with an oxo moiety, and bicyclic aromatic or non-aromatic ring systems. An example of a 5 membered heterocyclic group is thiazolyl, and an example of a 10 membered heterocyclic group is quinolinyl. Examples of non-aromatic heterocyclic groups are pyrrolidinyl, piperidino, morpholino, thiomorpholino and piperazinyl. Non-aromatic bicyclic heterocyclic groups include 8a-aza-bicyclo[3.2.1]octane. Examples of aromatic heterocyclic groups are pyridinyl, imidazolyl, pyrimidinyl, pyrazolyl, triazolyl, pyrazinyl, tetrazolyl, furyl, thienyl, isoxazolyl and thiazolyl. Heterocyclic groups having a fused benzene ring include benzimidazolyl.

The term "pharmaceutically acceptable salt(s)", as used herein, unless otherwise indicated, includes salts of acidic or basic groups that may be present in the compounds of formula 1. For example, pharmaceutically acceptable salts include sodium, calcium and potassium salts of carboxylic acid groups and hydrochloride salts of amino groups. Other pharmaceutically acceptable salts of amino groups are hydrobromide, sulfate, hydrogen sulfate, phosphate, hydrogen phosphate, dihydrogen phosphate, acetate, succinate, citrate, tartrate, lactate, mandelate, methanesulfonate (mesylate) and p-toluenesulfonate (tosylate) salts. The preparation of such salts is described below.

Certain compounds of formula 1 may have asymmetric centers and therefore exist in different enantiomeric forms. All optical isomers and stereoisomers of the compounds of formula 1, and mixtures thereof, are considered to be within the scope of the invention. With respect to the compounds of formula 1, the invention includes the use of a racemate, one or more enantiomeric forms, one or more diastereomeric forms, or mixtures thereof. The compounds of formula 1 may also exist as tautomers. This invention relates to the use of all such tautomers and mixtures thereof.

Patients that can be treated with compounds of formula 1, as defined above, or pharmaceutically acceptable salts or solvates thereof, according to the methods of this invention include, for example, patients that have been diagnosed as having lung cancer, bone cancer, pancreatic cancer, skin cancer, cancer of the head and neck, cutaneous or intraocular melanoma, uterine cancer, ovarian cancer, rectal cancer, cancer of the anal region, stomach cancer, colon cancer, breast cancer, gynecologic tumors (e.g., uterine sarcomas, carcinoma of the fallopian tubes, carcinoma of the endometrium, carcinoma of the cervix, carcinoma of the vagina or carcinoma of the vulva), Hodgkin's Disease, cancer of the esophagus, cancer of the small intestine, cancer of the endocrine system (e.g., cancer of the thyroid, parathyroid or adrenal glands), sarcomas of soft tissues, cancer of the urethra, cancer of the penis, prostate cancer, chronic or acute leukemia, solid tumors of childhood, lymphocytic lymphomas, cancer of the bladder, cancer of the kidney or ureter (e.g., renal cell carcinoma, carcinoma of the renal pelvis), or neoplasms of the central nervous system (e.g., primary CNS lymphoma, spinal axis tumors, brain stem gliomas or pituitary adenomas).

Patients that can be treated with compounds of formula 1 according to the methods of this invention also include patients suffering from abnormal cell growth, as defined above.

DETAILED DESCRIPTION OF THE INVENTION

The compounds of formula 1 are prepared as described below. In the reaction Scheme and discussion that follow, Z, R, $R^1$, $R^2$, $R^3$, and $R^4$ are as defined above.

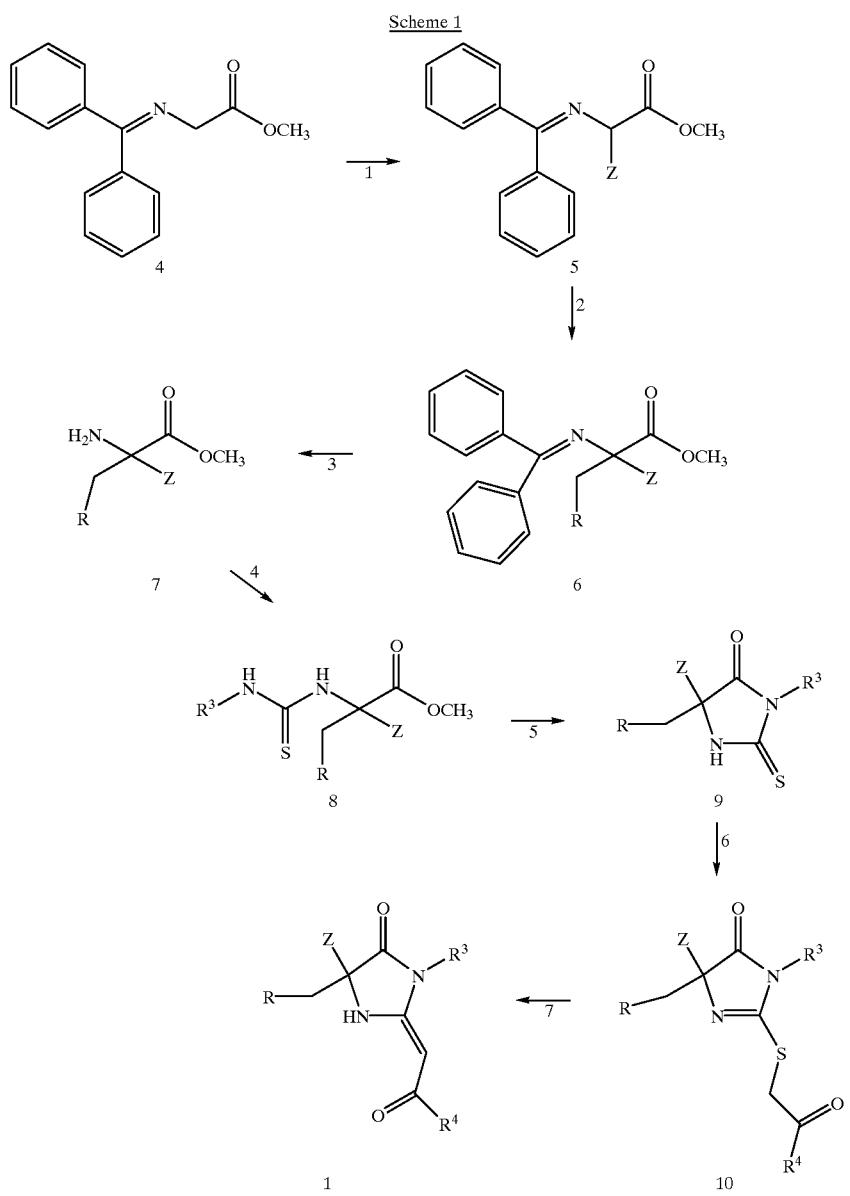
Scheme 1
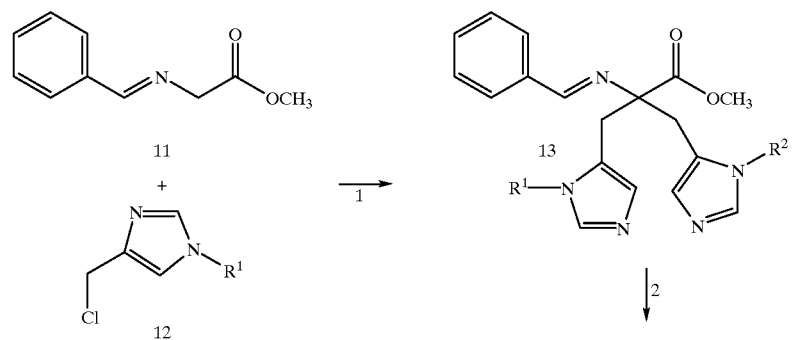
Scheme 2

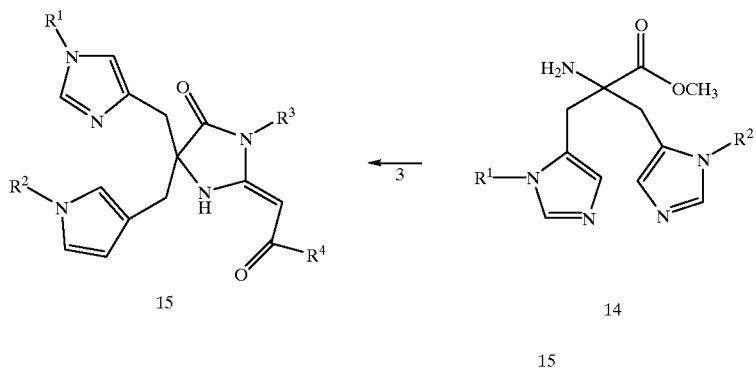

15

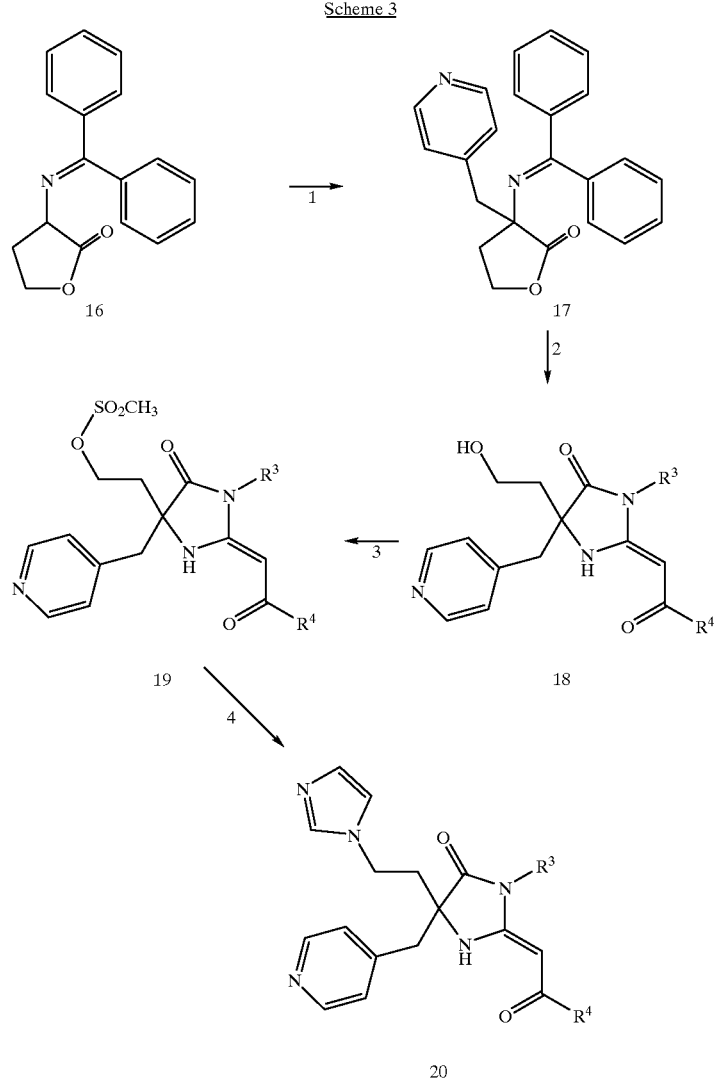

Scheme 1 illustrates the synthesis of the compounds of formula 1. In step 1, the ester of formula 4 is reacted with potassium bis(trimethylsilyl)amide in tetrahydrofuran (THF) at a temperature within the range of about −78° C. to 0° C. After stirring for about 30 minutes, a compound of the formula Z-X, wherein Z is as defined above and X is a leaving group such as chloro or bromo, is added to the reaction mixture, which is then allowed to warm to ambient temperature (20–25° C.). This results in the compound of formula 5, which can be isolated or reacted in situ to form the compound of formula 6. In step 2, a compound of the formula R—$CH_2$—X, wherein R is as defined above and X is a leaving group as defined for step 1, is added to the compound of formula 5 to provide the compound of formula 6 according to the procedure of step 1.

In step 3, the intermediate of formula 7 is formed by reacting the compound of formula 6 with an acid, preferably a mineral acid such as hydrochloric, nitric or sulfuric acid, in an organic co-solvent such as ethyl ether, THF or acetonitrile, preferably THF, at a temperature ranging from about −5° C. to 35° C., preferably from about 0° C. to ambient temperature.

Steps 4 and 5 may be done as a single step or as separate steps. In general, the intermediate of formula 9 is formed by reacting the intermediate of formula 7 with a compound of the formula $R^3$—NCS, wherein $R^3$ is as defined above. In this process, the intermediate of formula 7 and $R^3$—NCS are reacted in a protic solvent, such as methanol or ethanol, preferably ethanol, at a temperature ranging from about ambient temperature to 78° C., preferably at about the reflux temperature of the solvent. The reaction is preferably carried out for about 12 to 24 hours but this period can be longer or shorter depending on the $R^3$ substituent to be added. When $R^3$ is 1- or 2-adamantyl, it is preferable to use a large excess of the reactant $R^3$—NCS and to let the reaction proceed for a period of about two days to a week. For cases in which the intermediate of formula 8 is isolated prior to the formation of the intermediate of formula 9, a catalytic amount of potassium cyanide may be added to the reaction mixture to catalyze the formation of the intermediate of formula 9.

In step 6, the intermediate of formula 9 is reacted with a compound of the formula $R^4$—C(O)CH$_2$—X, wherein $R^4$ is as defined above and X is a leaving group, such as chloro or bromo, to provide the intermediate of formula 10. In this process, the intermediate of formula 9 is reacted with a strong base, such as sodium hydride, potassium tert-butoxide or potassium bis(trimethylsilyl)amide, preferably potassium bis(trimethylsilyl)amide, in a polar aprotic solvent such as THF, ethyl ether, dimethoxyethane (DME) or dimethylformamide (DMF), preferably THF, at a temperature ranging from about −78° C. to 35° C., preferably about 0° C. After stirring for about 30 minutes, the compound of formula $R^4$—C(O)CH$_2$—X is added to the reaction mixture and the mixture is then allowed to warm to ambient temperature. Alternatively, the intermediate of formula 9 is reacted with the compound of formula $R^4$—C(O)CH$_2$—X in a polar solvent, such as THF, DMF, acetonitrile or acetone, preferably acetone, in the presence of an acid scavenger, such as carbonate or an organic tertiary amine, preferably potassium carbonate. The reaction temperature is maintained between about −78° C. to 140° C., preferably between about 0° C. to ambient temperature, to provide the intermediate of formula 10.

In step 7, the compound of formula 1 is formed by treating the intermediate of formula 10 with a thiophile, such as triphenyl phosphine, tributyl phosphine or trimethylphosphite, preferably triphenyl phosphine, in a solvent such as toluene, benzene or pyridine, preferably toluene, at a temperature ranging from about 25° C. to 120° C., preferably about 100° C.

Scheme 2 illustrates a method of preparing compounds of formula 15 which are preferred compounds of formula 1. Scheme 2 essentially follows Scheme 1 using certain specific reagents. In step 1 of Scheme 2, the compound of formula 11 is reacted with the compound of formula 12, wherein $R^1$ is trityl, according to the procedure described above for step 1 of Scheme 1 to provide the compound of formula 13 wherein $R^1$ and $R^2$ are trityl. The compound of formula 13 is then converted to the compound of formula 14 according to step 3 of Scheme 1. Following the procedure of steps 4–7 of Scheme 1, the compound of formula 14 is converted to the compound of formula 15 wherein $R^1$ and $R^2$ are trityl. The trityl protecting groups may be removed with an acid, such as hydrochloric acid, in acetone or trifluoroacetic acid (TFA) and triethylsilane in methylene chloride.

Scheme 3 illustrates a method of preparing compounds of formula 20 which are also preferred compounds of formula 1. In step 1 of Scheme 3, the lactone of formula 16 is reacted with potassium bis(trimethylsilyl)amide in THF at a temperature of about −40° C. After stirring for about 30 minutes, 4-picolyl chloride is added to the reaction mixture and is then allowed to warm to ambient temperature (20–25° C.). This results in the compound of formula 17. Following the procedure of steps 3–7 of Scheme 1, the compound of formula 17 is converted into the compound of 18. In step 3 of Scheme 3, the compound of formula 18 is reacted with methanesulphonyl chloride and triethylamine in dichloromethane (CH$_2$Cl$_2$) to provide the compound of formula 19. In step 4 of Scheme 3, compound of formula 19 is reacted with imidazole in N,N-dimethylformamide (DMF) at about 80° C. to provide the compound of the formula 20 wherein $R^3$ and $R^4$ are as defined above.

The compounds of formula 1 that are basic in nature are capable of forming a wide variety of different salts with various inorganic and organic acids. Although such salts must be pharmaceutically acceptable for administration to animals, it is often desirable in practice to initially isolate the compound of formula 1 from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent, such as methanol or ethanol. Upon evaporation of the solvent, the desired solid salt is readily obtained. The desired acid addition salt can also be precipitated from a solution of the free base in an organic solvent by adding to the solution an appropriate mineral or organic acid. Cationic salts of the compounds of formula 1 are similarly prepared except through reaction of a carboxy group, such as where $R_5$ is carboxy, with an appropriate cationic salt reagent such as sodium, potassium, calcium, magnesium, ammonium, N,N'-dibenzylethylenediamine, N-methylglucamine (meglumine), ethanolamine, tromethamine, or diethanolamine.

The compounds of formula 1 and their pharmaceutically acceptable salts and solvates (hereinafter referred to, collectively, as "the therapeutic compounds") can be administered orally, transdermally (e.g., through the use of a patch), parenterally or topically. Oral administration is preferred. In general, compounds of the formula 1 and their pharmaceutically acceptable salts and solvates are most desirably administered in dosages ranging from about 1.0 mg up to about 500 mg per day, preferably from about 1 to about 100 mg per day in single or divided (i.e., multiple) doses. The therapeutic compounds will ordinarily be administered in daily dosages ranging from about 0.01 to about 10 mg per kg body weight per day, in single or divided doses. Variations may occur depending on the weight and condition of the person being treated and the particular route of administration chosen. In some instances, dosage levels below the lower limit of the aforesaid range may be more than adequate, while in other cases still larger doses may be employed without causing any harmful side effect, provided that such larger doses are first divided into several small doses for administration throughout the day.

The therapeutic compounds may be administered alone or in combination with pharmaceutically acceptable carriers or diluents by any of the routes previously indicated, and such administration may be carried out in single or multiple doses. More particularly, the novel therapeutic compounds of this invention can be administered in a wide variety of different dosage forms, i.e., they may be combined with various pharmaceutically acceptable inert carriers in the form of tablets, capsules, lozenges, troches, hard candies, powders, sprays, creams, salves, suppositories, jellies, gels, pastes, lotions, ointments, elixirs, syrups, and the like. Such carriers include solid diluents or fillers, sterile aqueous media and various non-toxic organic solvents, etc. Moreover, oral pharmaceutical compositions can be suitably sweetened and/or flavored.

For oral administration, tablets containing various excipients such as microcrystalline cellulose, sodium citrate, calcium carbonate, dicalcium phosphate and glycine may be employed along with various disintegrants such as starch (and preferably corn, potato or tapioca starch), alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration, solutions of a therapeutic compound in either sesame or peanut oil or in aqueous propylene glycol may be employed. The aqueous solutions should be suitably buffered if necessary and the liquid diluent first rendered isotonic. These aqueous solutions are suitable for intravenous injection purposes. The oily solutions are suitable for intra-articular, intramuscular and subcutaneous injection purposes. The preparation of all these solutions under sterile conditions is readily accomplished by standard pharmaceutical techniques well-known to those skilled in the art.

Additionally, it is also possible to administer the therapeutic compounds topically and this may preferably be done by way of creams, jellies, gels, pastes, ointments and the like, in accordance with standard pharmaceutical practice.

The therapeutic compounds may also be administered to a mammal other than a human. The dosage to be administered to a mammal will depend on the animal species and the disease or disorder being treated. The therapeutic compounds may be administered to animals in the form of a capsule, bolus, tablet or liquid drench. The therapeutic compounds may also be administered to animals by injection or as an implant. Such formulations are prepared in a conventional manner in accordance with standard veterinary practice. As an alternative the therapeutic compounds may be administered with the animal feedstuff and for this purpose a concentrated feed additive or premix may be prepared for mixing with the normal animal feed.

The compounds of formula 1 exhibit activity as Ras farnesylation inhibitors and are useful in the treatment of cancer and the inhibition of abnormal cell growth in mammals, including humans. The activity of the compounds of formula 1 as Ras farnesylation inhibitors may be determined by their ability, relative to a control, to inhibit Ras farnesyl transferase in vitro. This procedure is described below.

A crude preparation of human farnesyl transferase (FTase) comprising the cytosolic fraction of homogenized brain tissue is used for screening compounds in a 96-well assay format. The cytosolic fraction is prepared by homogenizing approx. 40 grams fresh tissue in 100 ml of sucrose/$MgCl_2$/EDTA buffer (using a Dounce homogenizer; 10–15 strokes), centrifuging the homogenates at 1000 g for 10 minutes at 4° C., re-centrifuging the supernatant at 17,000 g for 15 minutes at 4° C.,, and then collecting the resulting supernatant. This supernatant is diluted to contain a final concentration of 50 mM Tris HCl (pH 7.5), 5 mM DTT, 0.2 M KCl, 20 $\mu$M $ZnCl_2$, 1 mM PMSF and re-centrifuged at 235,000 g for 90 minutes at 4° C. The supernatant, termed "crude FTase" was assayed for protein concentration, aliquoted, and stored at −70° C.

The assay used to measure in vitro inhibition of human FTase is a modification of the method described by Amersham LifeScience for using their Farnesyl transferase (3H) Scintillation Proximity Assay (SPA) kit (TRKQ 7010). FTase enzyme activity is determined in a volume of 100 $\mu$l containing 50 mM N-(2-hydroxy ethyl) piperazine-N-(2-ethane sulfonic acid) (HEPES), pH 7.5, 30 mM $MgCl_2$, 20 $\mu$M KCl, 5 mM $Na_2HPO_4$, 5 mM dithiothreitol (DTT), 0.01% Triton X-100, 5% dimethyl sulfoxide (DMSO), 20 $\mu$g of crude FTase, 0.12 $\mu$M [3H]-farnesyl pyrophosphate ([3H]-FPP; 36000 dpm/pmole, Amersham LifeScience), and 0.2 $\mu$M of biotinylated Ras peptide KTKCVIS (Bt-KTKCVIS) that is N-terminally biotinylated at its alpha amino group and was synthesized and purified by HPLC in house. The reaction is initiated by addition of the enzyme and terminated by addition of EDTA (supplied as the STOP reagent in kit TRKQ 7010) following a 45 minute incubation at 37° C. Prenylated and unprenylated Bt-KTKCVIS is captured by adding 10 $\mu$l of streptavidin-coated SPA beads (TRKQ 7010) per well and incubating the reaction mixture for 30 minutes at room temperature. The amount of radio-activity bound to the SPA beads is determined using a MicroBeta 1450 plate counter. Under these assay conditions, the enzyme activity is linear with respect to the concentrations of the prenyl group acceptor, Bt-KTKCVIS, and crude FTase, but saturating with respect to the prenyl donor, FPP. The assay reaction time is also in the linear range.

The test compounds are routinely dissolved in 100% DMSO. Inhibition of farnesyl transferase activity is determined by calculating percent incorporation of tritiated-farnesyl in the presence of the test compound vs. its incorporation in control wells (absence of inhibitor). $IC_{50}$ values, that is, the concentration required to produce half maximal farnesylation of Bt-KTKCVIS, is determined from the dose-responses obtained.

The following Examples further illustrate the invention. In the following Examples, "Et" refers to ethyl, and "Ac" refers to acetyl.

EXAMPLE 1

4-{[4,4-Bis-(1H-imidazol-4-ylmethyl)-5-oxo-1-((−)-(2,6,6-trimethyl-bicyclo[3.1.1]hept-3-ylmethyl))-imidazolidin-2-ylidene]-acetyl}-benzonitrile 1A. 2-(Benzylidene-amino)-3-(1-trityl-1H-imidazol-4-yl)-2-(1-trityl-1H-imidazol-4-ylmethyl)-propionic acid methyl ester A solution of potassium bis(trimethylsilyl)amide (11.34 g, 54 mmol) in THF (100 ml) was added dropwise to a mixture of (benzylidene-amino)-acetic acid methyl ester (3.83 g, 21.63 mmol) and 4-chloromethyl-1-trityl-1H-imidazole (21.6 g, 60.18 mmol) in THF (200 ml) at −78° C. The resulting solution was warmed to ambient temperature and stirred for 24 hours. After removal of THF, the reaction mixture was subsequently partitioned between ethyl acetate and brine. The aqueous layer was washed two times with ethyl acetate. The ethyl acetate extracts were combined, dried over $MgSO_4$, filtered and concentrated to give the crude title compound of example 1A.

1B. 2-Amino-3-(1-trityl-1H-imidazol-4-yl)-2-(1-trityl-1H-imidazol-4-ylmethyl)-propionic acid methyl ester The crude title compound of example 1A was dissolved in anhydrous THF (40 ml). To the reaction was added 10 ml of a solution of 2.0 M aqueous hydrochloric acid (HCl) at 0° C. The mixture was stirred at ambient temperature for two hours. The reaction was subsequently concentrated under vacuum to remove the THF. The reaction mixture was then partitioned between ethyl ether and water. The aqueous layer was washed two more times with ethyl ether. The pH of the aqueous layer was then adjusted to 9 with sodium carbonate ($Na_2CO_3$) and the solution was extracted with methylene chloride until virtually no product was left in the methylene chloride ($CH_2Cl_2$) layer. The $CH_2Cl_2$ extracts were combined, dried over $MgSO_4$, filtered and concentrated under vacuum to give the crude product. The crude product was chromatographed on silica gel with $CH_3OH$—$CHCl_3$—$NH_4OH$ (1:99:0.1) as eluents to afford the title compound of example 1B as a white foam, 10.78 g (14.7 mmol, 68% yield for two steps).

1C. 2-Thioxo-3-(2,6,6-trimethyl-bicyclo[3.1.1]hept-3-ylmethyl)-5,5-bis-(1-trityl-1H-imidazol-4-ylmethyl)-imidazolidin-4-one The reaction mixture of the title compound of example 1B (0.277 g, 0.38 mmol) and (−)-3-pinanemethyl isothiocyanate (0.48 g, 2.27 mmol) in ethanol (2 ml) was heated to reflux overnight under an atmosphere of dry $N_2$. It was then poured into 10% $K_2CO_3$ aqueous solution and extracted with $CH_2Cl_2$. The organic layer was washed with brine, dried over $MgSO_4$ and concentrated to afford the crude product. The crude product was chromatographed on silica gel with $CH_3OH$—$CHCl_3$—$NH_4OH$ (2:98:0.1) to (5:95:1) as eluents to afford the title compound of example 1C as a white solid, 0.108 g (119 mmol, 31% yield).

Cl-MS: m/e 911.5 [M+1].

1D. 4-{[5-Oxo-1-(2,6,6-trimethyl-bicyclo[3.1.1]hept-3-ylmethyl)-4,4-bis-(1-trityl-1H-imidazol-4-ylmethyl)-4,5-dihydro-1H-imidazol-2-ylsulfanyl]-acetyl}-benzonitrile The title compound of example 1C (94 mg, 0.103 mmol) in anhydrous THF (1.0 ml) was added to a solution of potassium bis(trimethylsilyl)-amide (24 mg, 0.114 mmol) in THF (1 ml) at −78° C. The mixture was warmed to room temperature and stirred for 15 minutes, 4-cyanophenacyl bromide (25 mg, 0.114 mmol) was added and the reaction was stirred at ambient temperature overnight. The mixture was subsequently partitioned between $CH_2Cl_2$ and saturated sodium bicarbonate ($NaHCO_3$) solution. The $CH_2Cl_2$ layer was washed with brine, dried over $MgSO_4$ and concentrated under vacuum to give the crude title compound (107 mg, 0.101 mmol, 98% yield).

Cl-MS: m/e 812.4 [M$^+$-trityl].

1E. 4-{[5-Oxo-1-(2,6,6-trimethyl-bicyclo[3.1.1]hept-3-ylmethyl)-4-[1-(2,2,2-triphenyl-ethyl)-1H-imidazol-4-ylmethyl]-4-(1-trityl-1H-imidazol-4-ylmethyl)-imidazolidin-2-ylidene]-acetyl}-benzonitrile The crude title compound of example 1D (107 mg, 0.101 mmol) was dissolved in anhydrous toluene (10 ml) under an atmosphere of $N_2$. To the solution was added triphenylphosphine (79.4 mg, 0.303 mmol). The reaction was subsequently heated to 100° C. After stirring for 40 hours, the reaction was concentrated under vacuum and then partitioned between 0.1 N HCl and ethyl ether. The aqueous layer was washed two times with ethyl ether and subsequently adjusted to pH 8 with $K_2CO_3$. The product was then extracted into $CH_2Cl_2$, dried over $Na_2SO_4$, filtered and concentrated under vacuum to give 101 mg of the crude title compound of example 1 E.

Cl-Ms: m/z 780.5 [M$^+$-trityl].

1F. 4-{[4,4-Bis-(1H-imidazol-4-ylmethyl)-5-oxo-1-(2,6,6-trimethyl-bicyclo[3.1.1]hept-3-ylmethyl)-imidazolidin-2-ylidene]-acetyl}-benzonitrile To a solution of the title compound of 1E (0.101 g, 0.108 mmol) in $CH_2Cl_2$ (1 ml) was added $NH_4F$ (0.010 g, 0.43 mmol) and triethylsilane (0.069 ml, 0.43 mmol) followed by addition of 2 ml TFA. The reaction mixture was stiired at ambient temperature for 12 h. It was partitioned between $CH_2Cl_2$ and saturated sodium bicarbonate ($NaHCO_3$) solution. The $CH_2Cl_2$ layer was dried over $MgSO_4$, filtered, and concentrated under vacuum to give the crude product. The crude product was chromatographed on silica gel with $CH_3OH$—$CHCl_3$—$NH_4OH$ (6:94:0.1) as eluents to afford the title compound of example 1, 10 mg (0.019 mmol, 19% yield for two steps).

Cl-MS: m/z 538.3 [M+1].

EXAMPLE 2

4-{[4,4-Bis-(1H-imidazol-4-ylmethyl)-5-oxo-1-((+)-(2,6,6-trimethyl-bicyclo[3.1.1]hept-3-ylmethyl))-imidazolidin-2-ylidene]-acetyl}-benzonitrile Using the same procedure as described in example 1, (+)-3-pinanemethyl isothiocyanate (0.463 mmol) was used in the place of (−)-3-pinanemethyl isothiocyanate. After cyclization with 2-amino-3-(3-methyl-3H-imidazol-4-yl)-2-(3-methyl-3H-imidazol-4-ylmethyl)-propionic acid methyl ester (0.463 mmol), sulfur-alkylation of 4-cyanophenacyl bromide in the presence of potassium bis(trimethylsilyl) amide and sulfur-extrusion in the presence of triphenylphosphine, 2.4 mg of the title compound was obtained as a white solid.

Cl-MS: m/z 538.3 [M+1].

EXAMPLE 3

4-{[4,4-Bis-(3-methyl-3H-imidazol-4-ylmethyl)-5-oxo-1-(−)(2,6,6-trimethyl-bicyclo[3.1.1]hept-3-ylmethyl)-imidazolidin-2-ylidene]-acetyl}-benzonitrile 3A. 2-(Benzhydrylidene-amino)-3-(3-methyl-3H-imidazol-4-yl)-2-(3-methyl-3H-imidazol-4-ylmethyl)-propionic acid methyl ester Using the same procedure as described in example 1A, the reaction of 4-chloromethyl-1-methyl-1H-imidazole (2.5 g, 12.5 mmol) and (benzhydrylidene-amino)-acetic acid methyl ester (1.056 g, 4.17 mmol) in the presence of potassium bis(trimethylsilyl)-amide (5.24g, 25.02 mmol) in THF yielded 1.40 g (3.181 mmol, 76% yield) of the title compound of example 3A after chromatographic purification.

3B. 2-Amino-3-(3-methyl-3H-imidazol-4-yl)-2-(3-methyl-3H-imidazol-4-ylmethyl)-propionic acid methyl ester Using the same procedure as described in example 1B, the title compound of example 3A (960 mg, 2.17 mmol) was treated with HCl in THF to afford 652 mg (77% yield) of the title compound of example 3B.

3C. 5,5-Bis-(3-methyl-3H-imidazol-4-ylmethyl)-2-thioxo-3-(2,6,6-trimethyl-bicyclo[3.1.1]hept-3-ylmethyl)-imidazolidin-4-one Using the same procedure as described in example 1C, a reaction mixture of the title compound of example 3B (0.22 g, 0.78 mmol) and (−)-3-pinanemethyl isothiocyanate (0.38 g, 1.80 mmol) was heated in ethanol (heated to reflux) to generate 0.355 g (0.78 mmol, 100% yield) of the title compound of example 3C after chromatographic purification.

Cl-MS: m/e 455.4 [M+1].

3D. 4-{[4,4-Bis-(3-methyl-3H-imidazol-4-ylmethyl)-5-oxo-1-(2,6,6-trimethyl-bicyclo[3.1.1]hept-3-ylmethyl)-4,5-dihydro-1H-imidazol-2-ylsulfanyl]-acetyl}-benzonitrile Using the same procedure as described in example 1D, the title compound of 3C (0.355 g, 0.78 mmol) and 4-cyanophenacyl bromide (193 mg, 0.86 mmol) in the presence of potassium bis(trimethylsilyl)-amide (193 mg, 0.86 mmol) reacted to yield 0.232 g (0.39 mmol, 50% yield) of the title compound of example 3D after chromatographic purification. Cl-Ms: m/z 598.3 [M+1].

3E. 4-{[4,4-Bis-(3-methyl-3H-imidazol-4-ylmethyl)-5-oxo-1-(2,6,6-trimethyl-bicyclo[3.1.1]hept-3-ylmethyl)-imidazolidin-2-ylidene]-acetyl}-benzonitrile Using the same procedure as described in example 1E, the title compound of 3D (0.232 g, 0.39 mmol) and triphenylphosphine (0.31 g, 1.16 mmol) in toluene (heated to reflux) yielded 0.130 g (0.23 mmol, 100% yield) of the title compound of example 3E after chromatographic purification. Cl-MS: m/z 566.3 [M+1].

EXAMPLE 4

4-{[4-(2-imidazol-1-yl-ethyl)-5-oxo-4-pyridin-4-ylmethyl-1-((+)-(2,6,6-trimethyl-bicyclo[3.1.1]hept-3-ylmethyl))-imidazolidin-2-ylidene]-acetyl}-benzonitrile 4A. 3-(Benzhydrylidene-amino)-dihydro-furan-2-one The hydrogen bromide salt of Q-amino-γ-butyrolactone (5.00 g, 27.5 mMol) was suspended in $CH_2Cl_2$ (50 mL) and stirred under an atmosphere of dry $N_2$. To this solution was added benzophenone imine (4.60 mL, 27.5 mMol) and the reaction mixture was stirred for 16 hours at ambient temperature. The mixture was filtered and the filtrate was concentrated under vacuum to give 6.81 g of the titled compound as an oil.

4B. 3-(Benzhydrylidene-amino)-3-pyridin-4-ylmethyl-dihydro-furan-2-one

Potassium bis-(trimethylsilyl)amide (2.67, 13.4 mMol) was dissolved in anhydrous THF (50 mL) under an atmosphere of dry $N_2$. The mixture was cooled to −40° C. to which was added a solution of 3-(benzhydrylidene-amino)-dihydro-furan-2-one (3.38 g, 12.7 mMol) in THF (30 mL). The mixture was warmed to ambient temperature and stirred at this temperature for 30 minutes. The solution was then cooled to −40° C. and a solution of 4-picolyl chloride (1.70 g, 13.4 mMol) in THF (20 mL) was added. The reaction mixture was warmed to ambient temperature and stirred for 18 hours. The mixture was partitioned between ethyl acetate-(EtOAc) and water. The organic layer was dried over sodium sulfate ($Na_2SO_4$), filtered and concentrated under vacuum to give a yellow oil. The oil was chromatographed on flash silica gel eluting with a gradient of EtOAc-hexanes (50:50) to EtOAc-hexanes (60:40 ) to give 2.26 g of the titled compound as an oil which crystallizes to a white solid upon standing.

4C. 3-Amino-3-pyridin-4-ylmethyl-dihydro-furan-2-one 3-(Benzhydrylidene-amino)-3-pyridin-4-ylmethyl-dihydro-furan-2-one (1.67 g, 4.69 mMol) was dissolved in a solution of 1 N HCl (20 mL) in THF (50 mL). The mixture was stirred for 1 hour at ambient temperature after which time it was partitioned between ethyl ether ($Et_2O$) and water. The water layer was washed again with $Et_2O$ and then adjusted to pH 8 with $NaHCO_3$. The aqueous layer was then extracted with $CH_2Cl_2$. The $CH_2Cl_2$ layer was dried over $Na_2SO_4$, filtered and concentrated under vacuum to give 630 mg of the titled compound as an oil.

4D. 5-(2-Hydroxy-ethyl)-5-pyridin-4-ylmethyl-2-thioxo-3-((+)-(2,6,6-trimethyl-bicyclo[3.1.1]hept-3-ylmethyl))-imidazolidin-4-one 3-Amino-3-pyridin-4-ylmethyl-dihydro-furan-2-one (630 mg, 3.28 mMol) and (+)-pinanemethyl isothiocyanate (1.37 g, 6.55 mMol) were dissolved in ethanol (20 mL) and heated to 80° C. The reaction mixture was stirred for 48 hours at this temperature and was then cooled to ambient temperature. Crystals slowly grew at room temperature. After 24 hours the mixture was filtered and the solid was washed with hexanes and dried under vacuum to give 548 mg of the titled compound as a white solid as a 1:1 mixture of diastereomers.

4E. 4-{[4-(2-Hydroxy-ethyl)-5-oxo-4-pyridin-4-ylmethyl-1-((+)-(2,6,6-trimethyl-bicyclo[3.1.1]hept-3-ylmethyl))-4,5-dihydro-1H-imidazol-2-ylsulfanyl]-acetyl}-benzonitrile Potassium bis-(trimethylsilyl)amide (286 mg, 1.43 mMol) was dissolved in anhydrous THF (20 mL) under an atmosphere of dry $N_2$. The mixture was cooled to −40° C. and then 5-(2-hydroxy-ethyl)-5-pyridin-4-ylmethyl-2-thioxo-3-((+)-(2,6,6-trimethyl-bicyclo[3.1.1]hept-3-ylmethyl))-imidazolidin-4-one (548 mg, 1.37 mMol) was added. The mixture was warmed to ambient temperature and 4-cyanophenacyl bromide (350 mg, 1.43 mMol) was added. The reaction mixture was stirred for one hour after which time it was partitioned between $CH_2Cl_2$ and saturated aqueous $NaHCO_3$ solution. The $CH_2Cl_2$ layer was dried over $Na_2SO_4$, filtered and concentrated under vacuum to give a red foam. The foam was chromatographed on flash silica gel eluting with EtOAc-hexanes (50:50) to give 700 mg of the titled compound as a yellow foam as a 1:1 mixture of diastereomers.

4F. 4-{[4-(2-Hydroxy-ethyl)-5-oxo-4-pyridin-4-ylmethyl-1-((+)-(2,6,6-trimethyl-bicyclo[3.1.1]hept-3-ylmethyl))-imidazolidin-2-ylidene]-acetyl}-benzonitrile 4-{[4-(2-Hydroxy-ethyl)-5-oxo-4-pyridin-4-ylmethyl-1-((+)-(2,6,6-trimethyl-bicyclo[3.1.1]hept-3-ylmethyl))-4,5-dihydro-1H-imidazol-2-ylsulfanyl]-acetyl}benzo-nitrile (700 mg, 1.29 mMol), and triphenyl phosphine (1.34 g, 5.11 mMol) were dissolved in 100 mL of anhydrous toluene under an atmosphere of dry $N_2$. The solution was heated to 100° C. and stirred at this temperature for 24 hours. The reaction mixture was concentrated under vacuum and partitioned between $Et_2O$ and 0.1 N aqueous HCl solution. The aqueous layer was washed with $Et_2O$ and then was adjusted to pH 8 with $NaHCO_3$. The mixture was extracted with $CH_2Cl_2$. The $CH_2Cl_2$ layer was dried over $Na_2SO_4$, filtered and concentrated under vacuum to give 280 mg of the titled compound as a tan foam as a 1:1 mixture of diastereomers.

4G. Methanesulfonic acid 2-[2-[2-(4-cyano-phenyl)-2-oxo-ethylidene]-5-oxo-4-pyridin-4-ylmethyl-1-((+)-(2,6,6-trimethyl-bicyclo[3.1.1]hept-3-ylmethyl))-imidazolidin-4-yl]-ethyl ester 4-{[4-(2-Hydroxy-ethyl)-5-oxo-4-pyridin-4-ylmethyl-1-((+)-(2,6,6-trimethyl-bicyclo[3.1.1]hept-3-ylmethyl))-imidazolidin-2-ylidene]-acetyl}-benzonitrile (1.76 g, 3.44 mMol) and diisopropylamine (0.90 mL, 5.16 mMol) were dissolved in $CH_2Cl_2$ (20 mL) under an atmosphere of dry $N_2$. To this solution was added methanesulfonyl chloride (0.41 mL, 5.16 mMol) and the mixture was stirred at ambient temperature for 20 minutes. The mixture was concentrated under vacuum and was partitioned between $Et_2O$-EtOAc (50:50) and water. The organic layer was washed succesively with saturated aqoueus $NaHCO_3$ solution, brine and then dried over $MgSO_4$, filtered and concentrated under vacuum to give the titled compound as an oil as a 1:1 mixture of diastereomers.

4H. 4-{[4-(2-Imidazol-1-yl-ethyl)-5-oxo-4-pyridin-4-ylmethyl-1-((+)-(2,6,6-trimethyl-bicyclo[3.1.1]hept-3-ylmethyl))-imidazolidin-2-ylidene]-acetyl}-benzonitrile Methanesulfonic acid 2-[2-[2-(4-cyano-phenyl)-2-oxo-ethylidene]-5-oxo-4-pyridin-4-ylmethyl-1-((+)-(2,6,6-trimethyl-bicyclo[3.1.1 ]hept-3-ylmethyl))-imidazolidin-4-yl]-ethyl ester (300 mg, 0.508 mMol) and imidazole (102 mg, 1.5 mMol) were dissolved in anhydrous dimethylformamide (2 mL) under an atmosphere of dry $N_2$. To this mixture was added $K_2CO_3$ (207 mg, 1.5 mMol). The mixture was heated to 80° C. for 24 hours after which time it was cooled to ambient temperature and subsequently concentrated under vacuum. The residue was partitioned between $CH_2Cl_2$ and water. The $CH_2Cl_2$ layer was dried over $Na_2SO_4$, filtered and concentrated under vacuum to give a foam. The foam was chromatographed on flash silica gel using a gradient of $CHCl_3$—$CH_3OH$ (98:2) to $CHCl_3$—$CH_3OH$ (96:4) to give 190 mg of the titled compound as a 1:1 mixture of diastereomers: C.I. m/z 563.4 [M+1]; 1HNMR (CDCl3) δ8.42 (m, 4H), 7.86 (m, 4H), 7.74 (m, 4H), 7.38 (s, 1H), 7.31 (s, 1H), 7.06 (m, 4H), 7.04 (s, 1H), 7.02 (s, 1H), 6.88 (s, 1H), 6.84 (s, 1H), 5.50 (s, 1H), 5.45 (s, 1H), 3.80–4.10 (m, 4H), 2.90–3.35 (m, 8H), 2.60 (m 2H), 2.26 (m, 4H), 1.20–2.00 (m, 14H), 1.15 (s, 3H), 1.14 (s, 3H), 1.04 (m, 6H), 0.90 (s, 3H), 0.84 (s, 3H).

EXAMPLE 5

4-{[1-Adamantan-1-ylmethyl-4,4-bis-(3-methyl-3H-imidazol-4-ylmethyl)-5-oxo-imidazolidin-2-ylidene]-acetyl}-benzonitrile Using the same procedure as described in example 3,1-isothiocyanato-methyl-adamantane (2.44 mmol) was used in the place of (–)-3-pinanemethyl isothiocyanate. After cyclization with 2-amino-3-(3-methyl-3H-imidazol-4-yl)-2-(3-methyl-3H-imidazol-4-ylmethyl)-propionic acid methyl ester, sulfur-alkylation of 4-cyanophenacyl bromide in the presence of potassium bis(trimethylsilyl)amide (as described in 1 D) and sulfur-extrusion in the presence of triphenylphosphine (as described in 1 E), 103 mg of the title compound was obtained as a white solid.

CI-MS: m/z 564.3 [M+1].

What is claimed is:
1. A compound of the formula 1

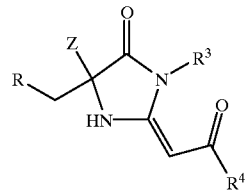

or a pharmaceutically acceptable salt or solvate thereof, wherein:
  Z is —$(CH_2)_n$—(imidazol-1-yl) wherein n is 1 or 2 or Z is a group of the formula

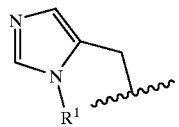

R is a group of the formula

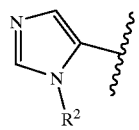

$R^1$ and $R^2$ are each independently selected from the group consisting of H, $C_1$–$C_{10}$ alkyl, —$(CH_2)_t(C_6$–$C_{10}$ aryl), wherein t is an integer ranging from 0 to 5, the —$(CH_2)_t$— moieties of the foregoing $R^1$ and $R^2$ groups optionally include a carbon—carbon double or triple bond where t is an integer between 2 and 5, and the foregoing $R^1$ and $R^2$ groups, other than H, are optionally substituted by 1 to 3 $R^5$ substituents;
  $R^3$ is —$(CH_2)_m(C_6$–$C_{10}$ aryl), $C_1$–$C_{15}$ alkyl,

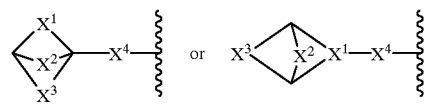

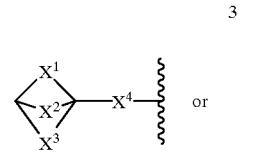

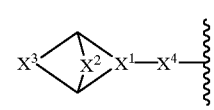

wherein m is an integer ranging from 0 to 6;
  $X^1$, $X^2$, and $X^3$ are each independently $C_1$–$C_7$ alkylene optionally containing 1 or 2 double or triple bonds where said alkylene contains at least two carbon atoms,
  $X^4$ is a bond or $C_1$–$C_7$ alkylene optionally containing 1 or 2 double or triple bonds where said alkylene contains at least two carbon atoms, and, in formula 3, the $X^4$ moiety is attached to the $X^1$ moiety at any available carbon in the $X^1$ moiety's alkylene chain;

$R^4$ is $C_1$–$C_6$ alkyl, or —$(CH_2)_t(C_6$–$C_{10}$ aryl), wherein said t is an integer ranging from 0 to 5 and said $R^4$ groups are optionally substituted by 1 to 3 $R^5$ substituents;

each $R^5$ is independently selected from the group consisting of $C_6$–$C_{10}$ aryl, and $C_1$-$C_4$ alkyl optionally substituted by 1 to 3 fluoro substituents, wherein the aryl groups are optionally substituted by 1 or 2 groups independently selected from halo, nitro, cyano, —C(O)OR$^6$, —SO$_2$NR$^6$R$^8$, —NR$^6$R$^8$, —C(O)R$^6$, —OR$^6$, and —S(O)$_n$(C$_1$–C$_6$ alkyl) wherein n is 0 to 2;

each $R^6$ is independently hydrogen or $C_1$–$C_6$ alkyl;

each $R^7$ is independently selected from cyano, —OR$^6$, —OC(O)R$^6$, —C(O)OR$^6$, —C(O)NR$^6$R$^8$, —NR$^6$R$^8$, —SO$_2$NR$^6$R$^8$, and $C_1$–$C_6$ alkyl optionally substituted by hydroxy or up to three halo groups; and, each $R^8$ is independently $R^6$ or —OR$^6$.

2. A compound according to claim 1 wherein Z is a group of the formula

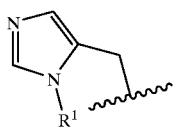

R is a group of the formula

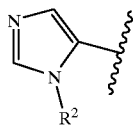

and $R^1$ and $R^2$ are each independently selected from H and C$_1$–C6 alkyl.

3. A compound according to claim 2 wherein $R^1$ and $R^2$ are each independently selected from H and methyl.

4. A compound according to claim 1 wherein wherein $R^3$ is

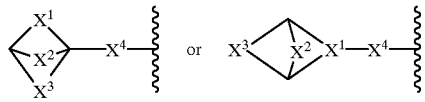

-continued

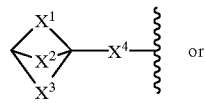

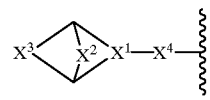

wherein X$^1$, X$^2$, X$^3$, and X$^4$ are as defined in claim 1.

5. A compound according to claim 4 wherein $R^3$ is 2,6,6-trimethyl-bicyclo hept-3-ylmethyl.

6. A compound according to claim 1 wherein $R^4$ is phenyl optionally substituted by 1 to 3 $R^5$ substituents, wherein $R^5$ is defined as in claim 1.

7. A compound according to claim 1 wherein said compound is selected from the group consisting of:

4-{[4,4-Bis-(1H-imidazol-4-ylmethyl)-5-oxo-1-((−)-(2,6,6-trimethyl-bicyclo[3.1.1]hept-3-ylmethyl))-imidazolidin-2-ylidene]-acetyl}-benzonitrile;

4-{[4,4-Bis-(1H-imidazol-4-ylmethyl)-5-oxo-1-((+)-(2,6,6-trimethyl-bicyclo[3.1.1]hept-3-ylmethyl))-imidazolidin-2-ylidene]-acetyl}-benzonitrile;

4-{[4-(2-Imidazol-1-yl-ethyl)-5-oxo-4-pyridin-4-ylmethyl-1-((+)-(2,6,6-trimethyl-bicyclo[3.1.1]hept-3-ylmethyl))-imidazolidin-2-ylidene]-acetyl}-benzonitrile;

and the pharmaceutically acceptable salts and solvates of the foregoing compounds.

8. A pharmaceutical composition for inhibiting abnormal cell growth in a mammal, comprising an amount of a compound according to claim 1 that is effective in inhibiting farnesyl protein transferase and a pharmaceutically acceptable carrier.

9. A pharmaceutical composition for inhibiting abnormal cell growth in a mammal, comprising an amount of a compound according to claim 1 that is effective in inhibiting abnormal cell growth and a pharmaceutically acceptable carrier.

* * * * *